(12) United States Patent
Gielen et al.

(10) Patent No.: US 7,803,164 B2
(45) Date of Patent: Sep. 28, 2010

(54) METHOD FOR GUIDING INSTRUMENTS HAVING DIFFERENT SIZES

(75) Inventors: Frans L. H. Gielen, Eckelrade (NL); Peter Appenrodt, Bremen (DE); Paulus Cornelis Van Venrooij, Hoensbroek (NL); Victor Duysens, Grevenbicht (NL)

(73) Assignee: Medtronic, Inc., Minneapolis, MN (US)

( * ) Notice: Subject to any disclaimer, the term of this patent is extended or adjusted under 35 U.S.C. 154(b) by 760 days.

(21) Appl. No.: 11/733,368

(22) Filed: Apr. 10, 2007

(65) Prior Publication Data

US 2008/0255583 A1 Oct. 16, 2008

(51) Int. Cl.
*A61B 19/00* (2006.01)

(52) U.S. Cl. ...................................... 606/130; 606/129

(58) Field of Classification Search .................. 606/129, 606/130; 600/201, 206, 207, 429
See application file for complete search history.

(56) References Cited

U.S. PATENT DOCUMENTS

| | | | |
|---|---|---|---|
| 5,221,264 A * | 6/1993 | Wilk et al. | 604/167.01 |
| 5,573,517 A * | 11/1996 | Bonutti et al. | 604/264 |
| 6,416,520 B1 | 7/2002 | Kynast et al. | |
| 6,482,182 B1 | 11/2002 | Carroll et al. | |
| 6,491,699 B1 | 12/2002 | Henderson et al. | |
| 6,493,573 B1 | 12/2002 | Martinelli et al. | |
| 6,516,212 B1 | 2/2003 | Bladen et al. | |
| 6,529,765 B1 * | 3/2003 | Franck et al. | 600/427 |
| 2003/0114752 A1 | 6/2003 | Henderson et al. | |
| 2004/0243146 A1 | 12/2004 | Chesbrough et al. | |
| 2005/0049486 A1 | 3/2005 | Urquhart et al. | |
| 2005/0085714 A1 | 4/2005 | Foley et al. | |
| 2005/0085720 A1 | 4/2005 | Jascob et al. | |
| 2006/0084867 A1 | 4/2006 | Tremblay et al. | |
| 2006/0122628 A1 * | 6/2006 | Solar et al. | 606/130 |
| 2006/0229641 A1 | 10/2006 | Gupta et al. | |

FOREIGN PATENT DOCUMENTS

WO WO-0217810 3/2002

OTHER PUBLICATIONS

"MicroTargeting Drive System for Stereotactic Positioning" FHC, Inc., Mar. 2006.
"Nexframe," 2 sheets printed from www.igneurologics.com on Jul. 9, 2007.
"MicroTargeting Drive System for Stereotactic Positioning: Precision Guidance using microelectrode recording", L022/Cat.p. 55-58 Rev.040927, 4 pgs.

* cited by examiner

*Primary Examiner*—Todd E Manahan
*Assistant Examiner*—Jonathan A Hollm
(74) *Attorney, Agent, or Firm*—Scott A. Marks; Harness, Dickey & Pierce, P.L.C.

(57) ABSTRACT

A system and procedure for using the system are disclosed for guiding instruments of varying sizes. The instruments can be guided into various portions of the anatomy for performing a procedure, providing a treatment, measuring a physiological response, or the like. Two or more instruments of varying sizes can be driven or guided relative to one another with the same system.

35 Claims, 10 Drawing Sheets

METHOD FOR GUIDING INSTRUMENTS HAVING DIFFERENT SIZES

CROSS-REFERENCE TO RELATED APPLICATIONS

This application is filed concurrently with U.S. patent application Ser. No. 11/733,362, entitled "SYSTEM FOR GUIDING INSTRUMENTS HAVING DIFFERENT SIZES." The disclosure of the above application is incorporated herein by reference.

FIELD

The present disclosure is directed to a system for a surgical procedure, and particularly to a system for guiding an instrument.

BACKGROUND

The statements in this section merely provide background information related to the present disclosure and may not constitute prior art.

A surgical procedure can be performed on various portions of an anatomy, such as a human anatomy. The surgical procedures can be invasive to varying degrees, such as by performing an open procedure or by performing a less invasive procedure. A procedure can be performed in a less invasive manner by minimizing or attempting to minimize an incision or portal formed in the tissue of the anatomy, opening through bone, and other minimization techniques.

A less invasive procedure, however, can also reduce visualization of a portion of the anatomy upon which a procedure is occurring, reduce access with various instruments to a portion of the anatomy, and the like. The less invasive procedure may also require specialized and particular instruments to perform a procedure in an appropriate and beneficial manner. It is desirable, therefore, to provide instruments, procedures, and the like to achieve an optimal outcome while maintaining the less invasive procedure.

Instruments, according to various applications, can be guided with exterior guide tools or systems to a selected portion of the anatomy to perform the procedure in the less invasive manner. For example, a scope can be guided along a selected portion of the anatomy for viewing an internal structure within the anatomy. Various other instruments can also be guided into the anatomy for various procedures. For example, in micro-electrode recording (MER) a micro-electrode (ME) can be guided into a portion of the anatomy, such as the brain, to record electrical activity therein. The recording of the electrical activity can be used for various diagnoses and identification procedures. A probe or deep brain stimulation (DBS) electrode or macro stimulation probe or lead can be guided in an area relative to the ME. The diameter of the ME and the DBS, however, can be different and the use of an identical guiding instrument may not be possible. Therefore, it is desirable to provide an instrument or system that is operable to guide instruments or tools having different sizes simultaneously, sequentially, or at selected times.

Generally known systems can require the use of additional and removable portions to accommodate different sized instruments. The additional pieces are generally small and require great dexterity and care for proper operation and use. The additional pieces may also require additional sterilization steps and care during transport and cleaning. Therefore, it may be desirable to provide a substantially complete system that can accommodate and work with different sized and shaped instruments.

SUMMARY

A system and method are disclosed for guiding instruments of varying sizes. The instruments can be guided into various portions of the anatomy for performing a procedure, providing a treatment, measuring a physiological response, or the like. The instruments can include micro-electrodes (ME), deep brain stimulation (DBS) probes, macro-electrode stimulation probes, cannulas, biopsy needles, or the like.

The system can allow instruments of various sizes to be guided relative to one another in an efficient manner. The instruments may be of varying sizes, but may be selected to be moved along substantially identical or similar trajectories. An instrument having a first size can be guided, removed, and a second instrument having a different size can be guided in a substantially identical trajectory. A guide tool or instrument can be provided to guide both of the instruments of varying sizes along the same or similar trajectories.

According to various embodiments, a system for guiding an instrument during a surgical procedure relative to an anatomy is disclosed. The system can include a guide fixture extending between a first end and a second end and also defining a height between a top edge and a bottom edge. A guide member can be associated with the guide fixture, the guide member can define a first movement portion and can define a first guide area. A movement section can be associated with the guide fixture. The movement section can be associated with the first movement portion of the guide member and adapted to allow movement of the guide member between a first position and a second position relative to the guide fixture. A second guide area can be defined by the guide fixture substantially aligned with said first guide area. The guide member in the first position defines the first guide area and the guide member in the second position is positioned to allow the instrument unrestricted access to the second guide area.

According to various embodiments, a system for guiding an instrument during a surgical procedure relative to an anatomy is disclosed. The system can include a drive system positioned relative to the anatomy. The drive system can include a drive section operable to drive an instrument into the anatomy from a drive area. The drive system can also include a guide fixture positioned relative to the drive section having a guide section positionable substantially aligned with the drive area of the drive section and a movement member extending from the guide fixture. A guide member can be operably connected to the movement member wherein the guide member is operable to move relative to the guide fixture from a first position to a second position. A first guide portion can be defined by the guide member wherein the guide portion is aligned with the drive section when the guide member is in the first position and a second guide portion can be defined by the guide section of the guide fixture substantially permanently aligned with the drive section. The first guide portion is operable to be aligned with the second guide portion when the guide member is in the first position.

According to various embodiments a system for guiding an instrument during a surgical procedure relative to an anatomy is disclosed. The system can include an elongated instrument operable to be driven into the anatomy and a drive section operable to drive the elongated instrument into the anatomy along a drive axis. A guide fixture can have a guide section with an internal point positioned near the drive axis. The system can also include a first guide area and a second guide area. The first guide area can be defined by at least two guide members operable to move between a close point near the internal point defined by the guide section and a far point displaced a distance from the internal point defined by the guide section. The first guide area is defined when at least two guide members are at the close point. The second guide area can be defined by passages formed in the guide section of the guide fixture. The first guide section and the second guide section can be aligned when the first guide section is defined by the least two guide members when positioned at the close point. The elongated instrument is operable to pass through both of said a first guide area and a second guide area along a single axis.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses. Moreover, although the following description is related to a procedure performed within a brain of a patient, the procedure within the brain is merely exemplary. Further, the discussion relating to the use of micro-electrodes for recording, deep brain stimulation probes (also referred to as leads or electrodes, biopsy needles, and the like within the brain are also merely exemplary. It will be understood that the disclosure herein can be used in any appropriate portion of the anatomy and during any appropriate procedure with any appropriate instrument.

Figure 2:
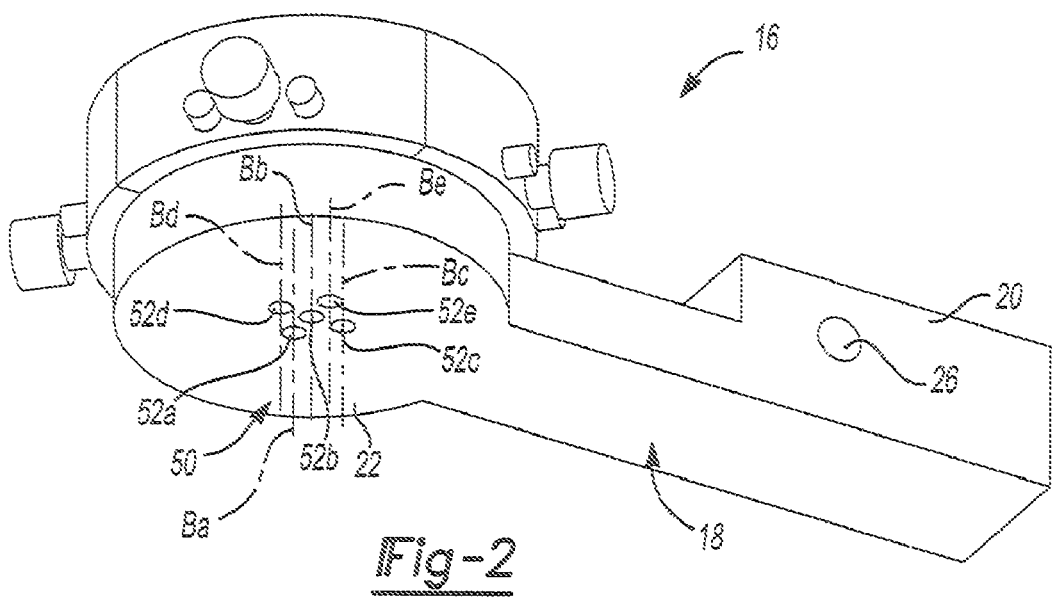
FIG. 2 is a bottom perspective close positioned view of a guide fixture, according to various embodiments.
Figure 3:
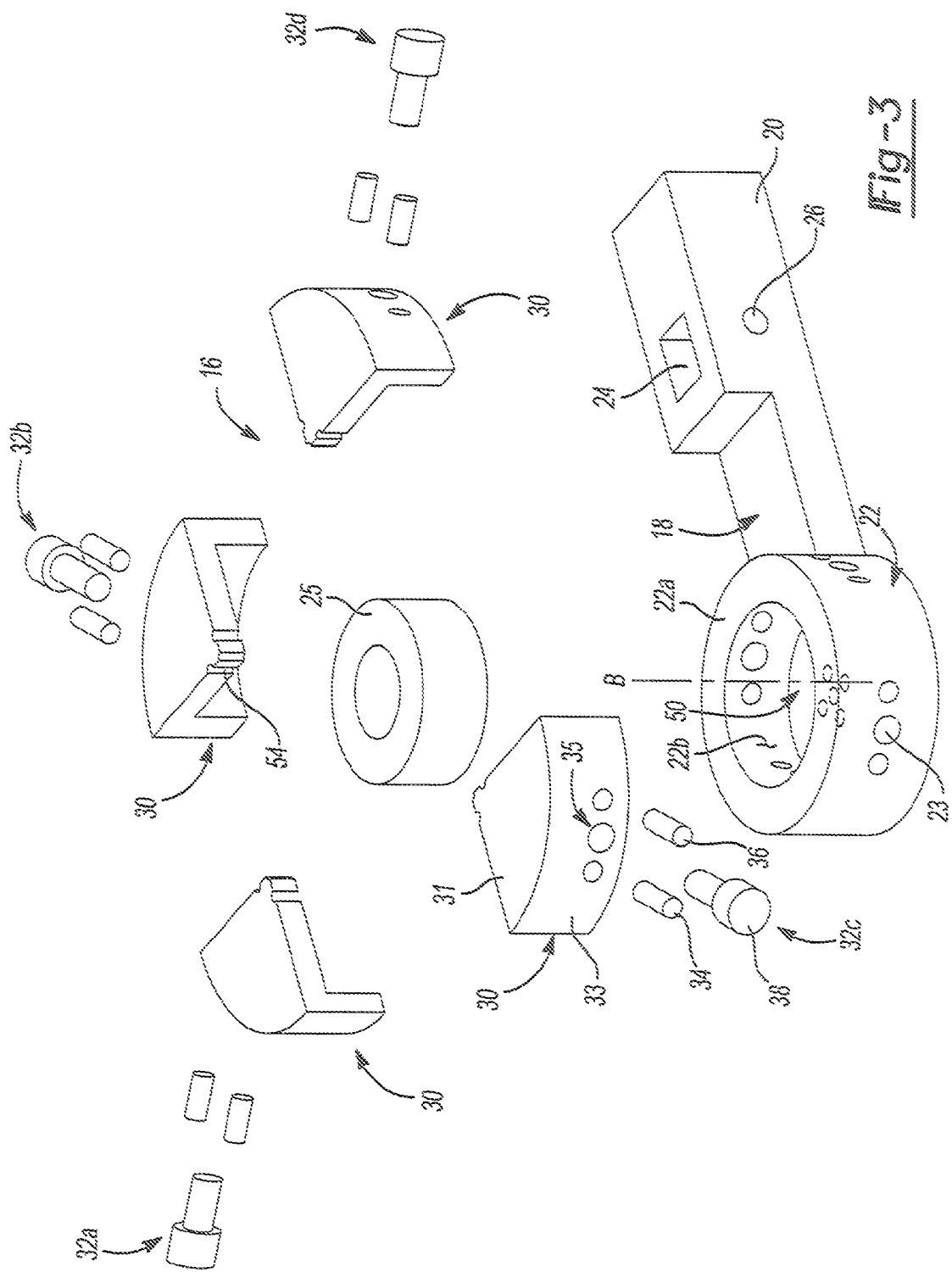
FIG. 3 is a top perspective exploded view of a guide fixture, according to various embodiments.
Figure 4:
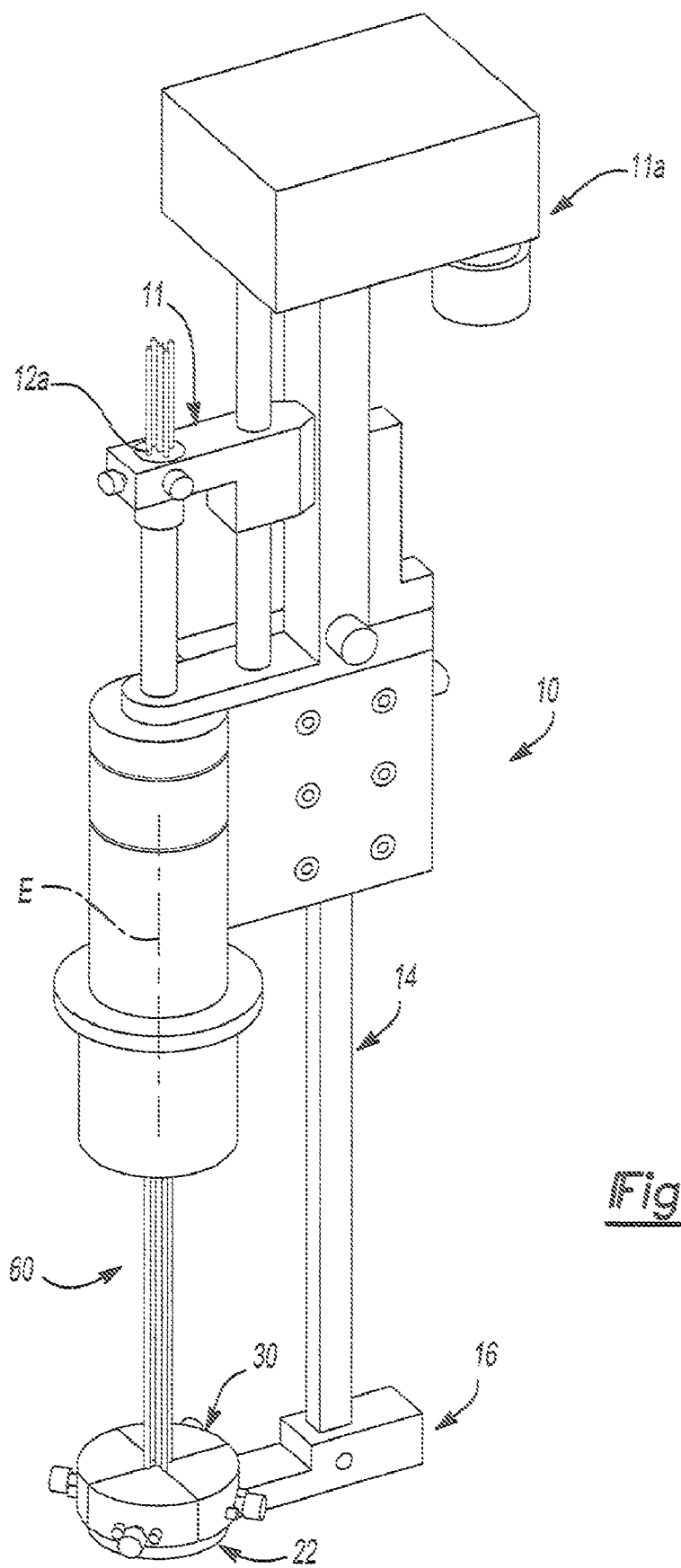
FIG. 4 is a detailed view of a drive system with a guide fixture, according to venous embodiments.
Figure 8:
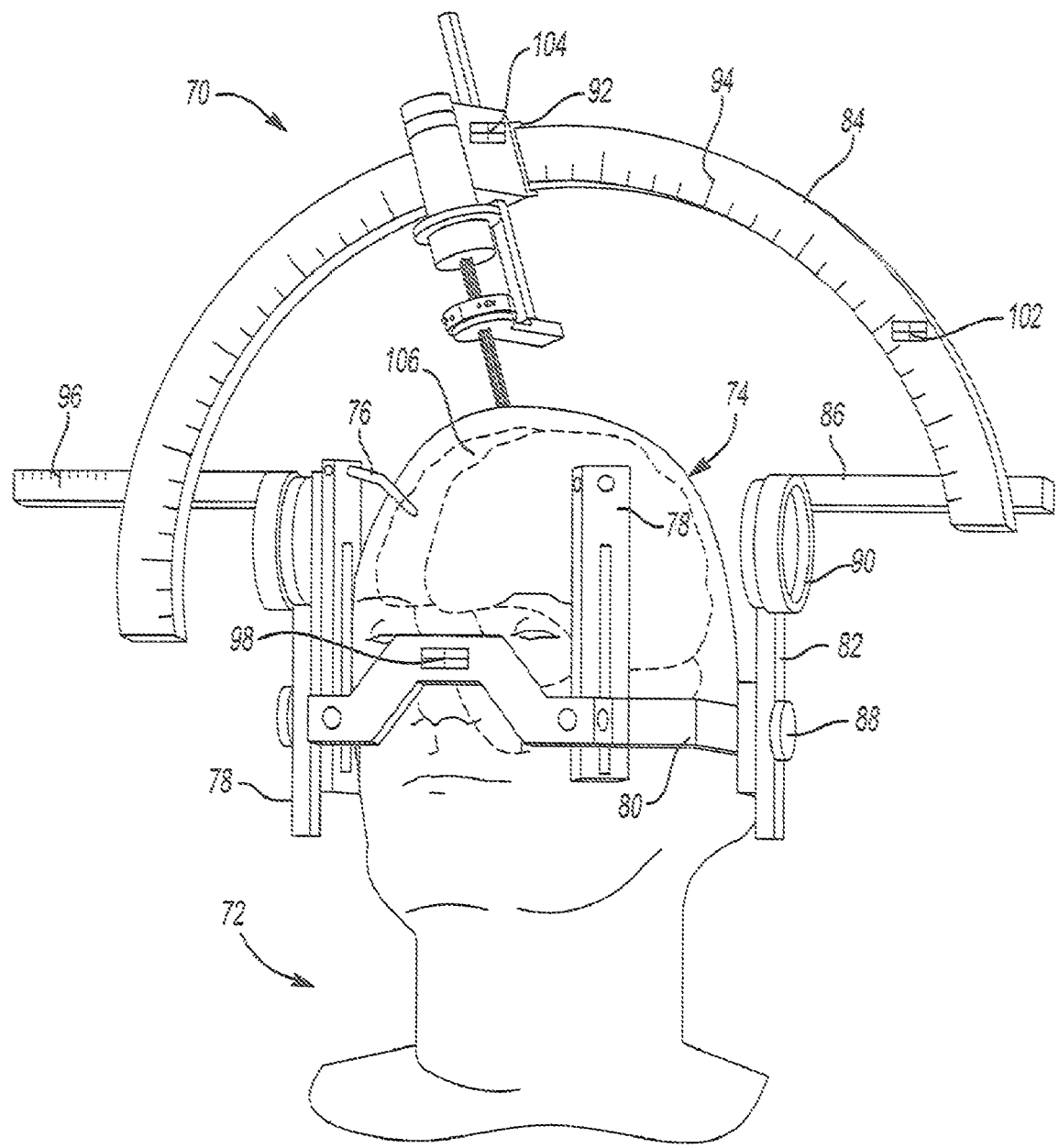
FIG. 8 is an environmental view of a drive system and support structure, according to various embodiments.
Figure 9:
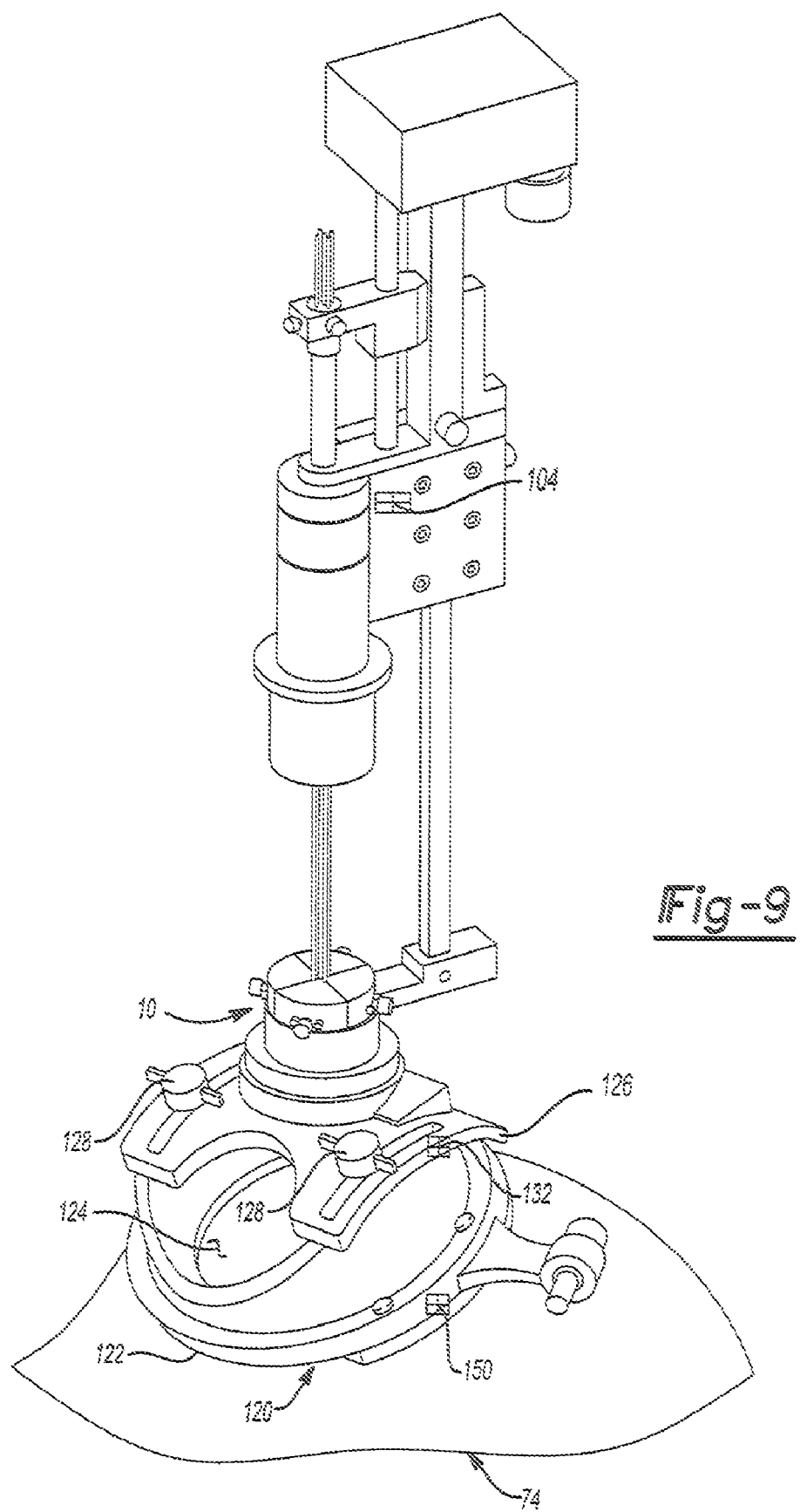
FIG. 9 is an environmental view of a drive system and support structure, according to various embodiments.

With reference to FIGS. 1-4, a guide or drive system 10 is illustrated, initially, with reference to FIG. 4, the drive system 10 can include any appropriate drive mechanism. The drive system 10 can include a drive or control portion 12, a connector rod or support 14, and a locomotion portion 11. The control portion 12, locomotion portion 11, and support portion 14 of the drive system 10 can include the microTargeting Drive® system produced by Fred Haer Corp., FHC Inc. 9 Main Street, Bowdoinham Me. 04008, USA. The drive system 10, as illustrated further herein, can be interconnected with various guide or support portions, including stereotactic head-frames 70 (FIG. 8), small-scale head-frames 120 (FIG. 9), robotic devices, or guide devices, to drive various instruments into selected portions of the anatomy. For example, the drive system 10 can be interconnected with head frames to position the drive system 10 at an appropriate location to drive various instruments into a cranium 74 (See FIG. 8). The instruments to be driven with the drive system 10 can include any appropriate instruments, including those examples discussed further herein. For example, the drive system 10 can drive micro-electrodes (ME), deep brain stimulation (DBS) electrodes, or other appropriate instruments.

The drive system 10 can also include a guide fixture or portion 16. The guide portion 16, however, cooperates with the drive portion 12 of the drive system 10 to drive the selected instruments into the appropriate portion of the anatomy, such as the cranium.

The drive system 10, in use, can be used to drive or move instruments through the drive portion 12 with the locomotion part 11. The locomotion part can be powered or manually drive to move the instrument holding section 12a. The support 14 can hold each of the portions of the drive system 10 during operation. The entire assembly can be operably connection to a head frame, as illustrated herein, to allow a user to drive the instruments into an anatomical portion, such as the cranium. One skilled in the art will understand that various gear trains and tracks can be used to transfer a force from the locomotion portion 11 to the holding section 12a.

The drive system 10 can be used to drive various instruments, such as ME's and DBS's into the brain. As will be discussed in more detail herein, a procedure on the brain can include a recorder for detecting electrical activity in the brain with the ME. Once a recording of the brain has occurred, a DBS can be delivered to an area identified with the ME. Generally, the ME, which can be used to identify a selected region of the brain, is removed and the DBS is driven and guided along a similar or identical trajectory or axis relative to the removed ME. The DBS can be provided to electrically stimulate the selected region of the anatomy, either short term or long term.

Figure 1:
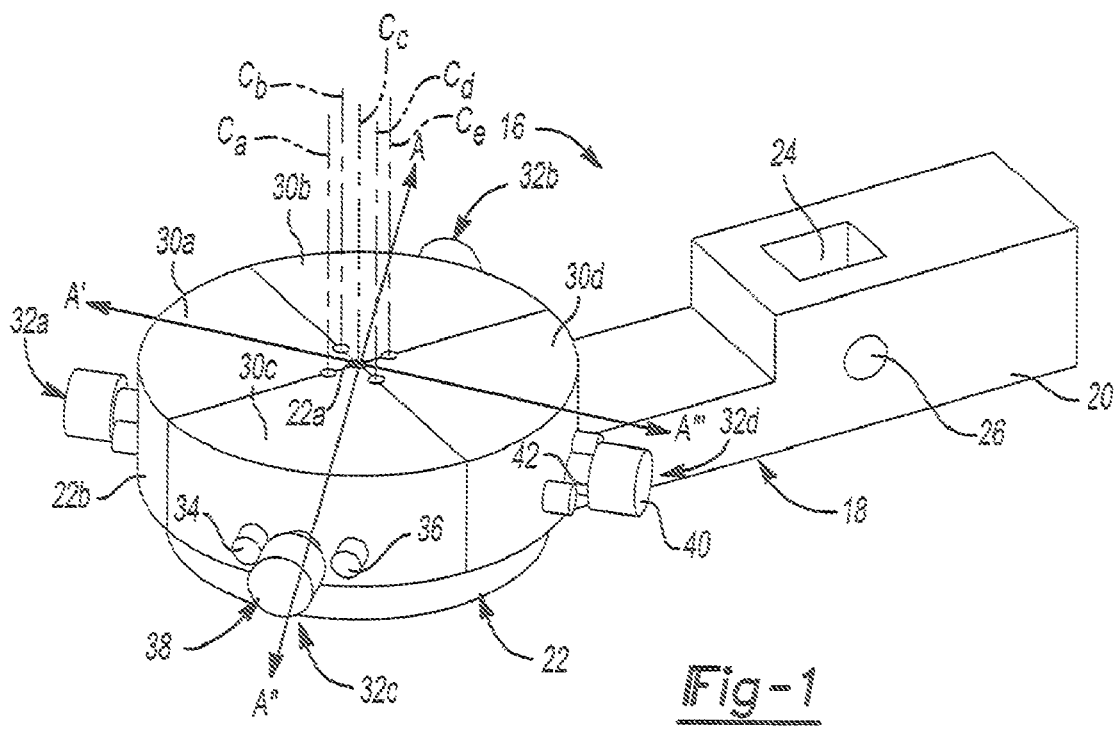
FIG. 1 is a top perspective close positioned view of a guide fixture, according to various embodiments.

The drive system 10 can cooperate with the guide portion 16, as illustrated in detail in FIGS. 1-3. The guide portion 16 can be formed of any appropriate material, or combination of materials. For example, the guide portion 16 can be formed of materials that can be sterilized, including titanium, stainless steel, metal alloys, or the like. Further, the guide portion 16 can be formed of substantially disposable materials, such as appropriate polymers. It will also be understood that the guide portion 16 can be formed of a combination of materials, such as metals that can be sterilized and disposable polymers, intended for one time use.

The guide portion 16 can include a base or arm portion or section 18. The base portion 18 can include an engagement leg 20 and a guide section 22. The engagement leg 20 can include or define an attachment section 24. The attachment section 24 can define a through bore or blind bore that is operable to engage the support 14. According to various embodiments, the support 14 can pass a selected distance into the attachment section 24 and a set screw 26 can be provided to securely and selectively engage the support 14. The set screw 26 can be provided as any appropriate engagement portion, which can include a clip, a threaded screw, a quick release connection, or any other appropriate connection mechanism.

The guide section 22 can extend away from the attachment arm 20 towards an axis E of the drive portion 12 (FIG. 4). It will be understood that the guide section 22 can include elements that can directly engage or slidingly engage instruments having different sizes or diameters to be guided into the anatomy. The guide section 22 is positioned relative to the drive portion 12 to guide instruments, as discussed herein, into an anatomy.

The guide section 22 can also be provided in any appropriate shape. The guide section 22 can be provided in a substantially circular or annular shape defined by an annular wall 22a. The guide section 22, however, can also be provided in a substantially polygonal configuration according to various embodiments.

The guide section can define passages 23 through the annular wall 22a. The passages 23 can extend completely through the wall 22a or can be formed only partially through the wall 22a. The passages 23 can provide a portion to interact with or hold the sliding section 32, discussed herein.

The guide section 22 can also define an internal well 22b. The internal well 22b can be partially filled with an auxiliary washer or annular member 25. The auxiliary washer 25 can also be substantially annular to mate with the wall 22a. The auxiliary washer 25 is provided to fill a portion of the well or void 22b. The auxiliary washer 25 can also provide a stop for the sliding members.

The guide section 22 can include various movable guide members or components 30. According to various embodiments four movable guide components 30 can be provided, and exemplary designated as 30a, 30b, 30c, and 30d. It will be understood that discussion of a particular guide component 30 can relate to each of the guide components, unless specifically discussed otherwise. The guide members 30 have a section wall or guide portion wall 31 and a partial annular or movement wall 33. The section wall 31 is formed to extend over the annular wall 22a of the guide section 22 and define a guide depression or portion 54, discussed herein. The partial annular wall 33 can engage the annular wall 22a and extend at an angle from the section wall 31, such as generally perpendicular thereto. The guide components 30 can be provided around the exemplary annular shape of the guide section 22 and can move along a selected axis, such as a longitudinal or radial axis of the guide section 22.

The guide members 30 can move along a set of radial axes A-A''' that extends from a center of the guide section 22 outward towards an outer edge 22b of the guide section 22. The guide members 30 can move to operably engage, such as guidingly or slidingly engage, various instruments as discussed further herein. The guide members 30 can also be moved to disengage selected guided instruments and allow for the engagement of selected guided instruments with other guide portions.

The guide members 30 can each define a movement or slide portion 35 and can slide along a track or slide portion 32. The movement portion 35 and the track portion 32 can operably define an adjustment mechanism. The slide portion 32 can include a first slide member 34, a second slide member 36, and a third slide member 38. The slide members 34, 36, and 38 can be smooth cylindrical guide posts. The slide portion 35 can include a number of passages complimentary to the number of slide members, such as three passages. It will be understood, however, that any appropriate number of slide members can be provided and three is merely exemplary. For example, two slide members can be provided, which allows for a guided sliding or movement of the guide members 30 while substantially eliminating rotation of the guide member 30 about any axis.

The slide portion 32, however, can also provide selected features. For example, the third slide member 38 can include an enlarged section or terminal portion 40 that defines a shoulder or stop section 42. The shoulder or stop section 42 can engage the guide member 30 as the guide member slides along the slide portion 32.

According to various embodiments, the third slide member 38, or any appropriate of the slide members 34-38, can move relative to the guide section 22. The third slide member 38 can define an exterior thread. The exterior thread can be complimentary to an internal thread defined by the movement portion 35 of the guide member 30. Rotating the third slide member 38 can, therefore, selectively move the guide member 30 along the radial axes A-A'''.

In addition, it will be understood that the slide section 32 can include a plurality of slide sections 32, exemplary illustrated as 32a, 32b, 32c, and 32d. The slide sections 32a-32d can be provided with respective guide members 30a-30d. Discussion of one of the slide sections 32 will be understood to be a discussion of each of the slide sections 32, unless specifically indicated otherwise.

The various portions, such as the slide members 34, 36, and 38 can be formed of any appropriate material, which may or may not be the same material as the guide portion 16. For example, the slide section 32 can be formed of an appropriate rigid polymer, metal or metal alloy, or combinations thereof. Further, the slide section 32 can be provided substantially immovable or removable relative to the guide section 22.

Figure 5:
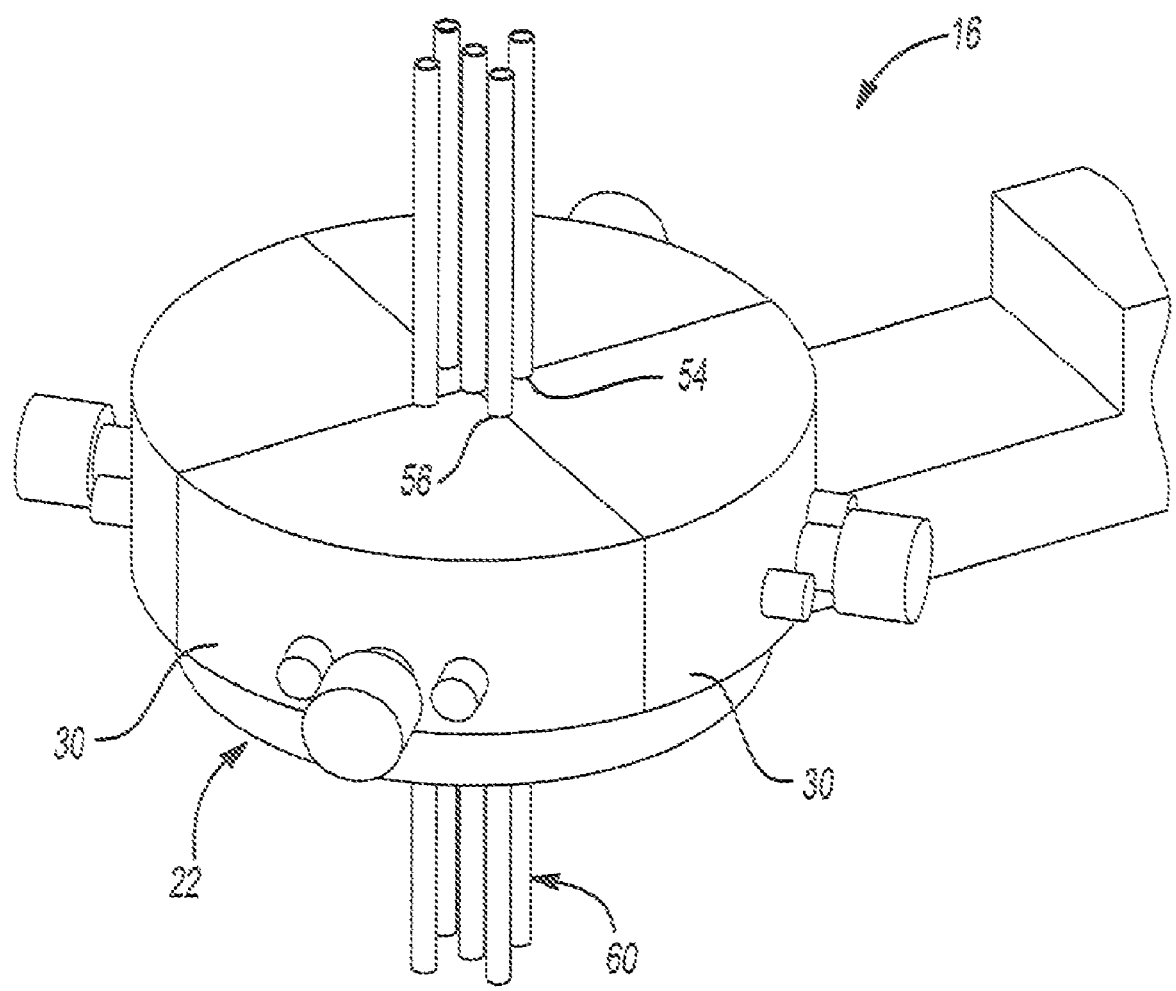
FIG. 5 is an environmental exemplary view of a guide fixture guiding instrument, according to various embodiments.
Figure 6:
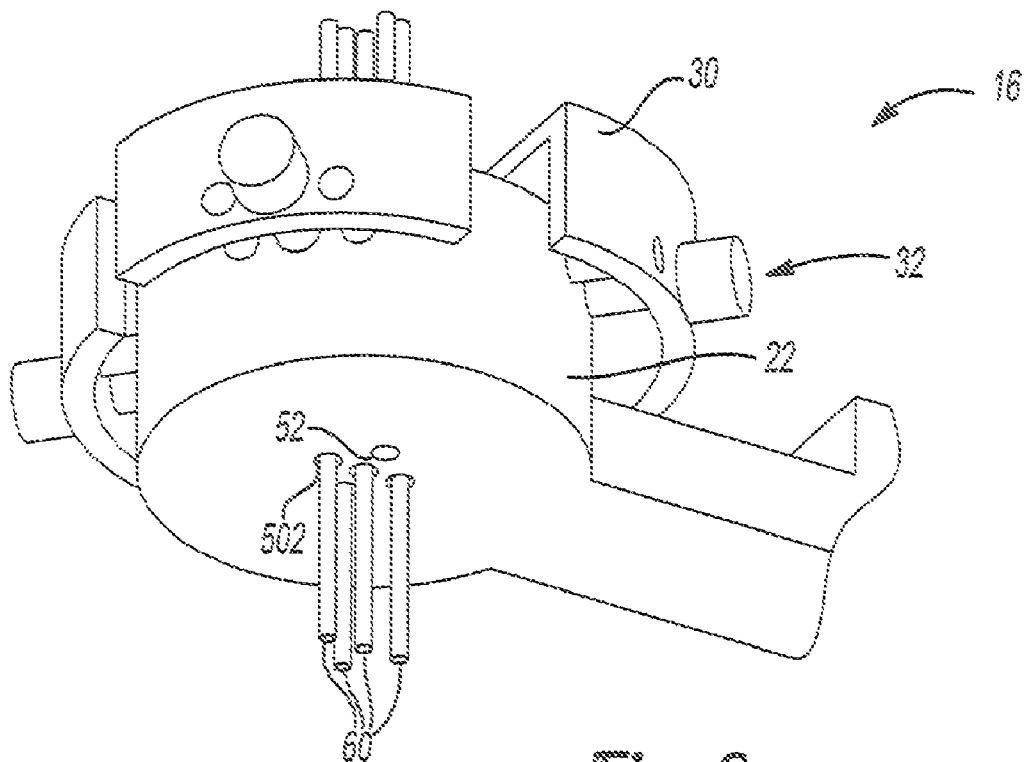
FIG. 6 is a fop perspective view of a guide fixture in a second position, according to various embodiments.

With reference to FIGS. 3 and 5-6, the guide section 22 can include an instrument guiding area 50 that can define one or more guide bores 52. As exemplary illustrated, a plurality of guide bores 52 can be included, such as 52a, 52b, 52c, 52d, and 52e. The guide bores 52 can be formed in the guide section 22 in any appropriate manner. For example, the guide section 22 can be formed as a solid piece and the guide bores 52 can be dried through, cut through, or formed in any appropriate manner. The guide bores 52, however, can be formed in the guide section 22 to guide a selected instrument having a selected dimension. For example, the guide bore 52 can include a diameter that allows for appropriate guiding of a relatively large instrument, such as a DBS probe or lead. The guide bores 52 can be formed in any appropriate size, but can be formed to have a substantially fixed size relative to the guide fixture 16. Each of the guide bores 52 also define a first set of guide axes B, or Ba, Bb, Bc, Bd, and Be respectively.

The guide members 30, with reference to FIG. 3, can include one or more guide portions or depressions 54 defined by a wall of the guide member 30. Each of the guide members 30 can include one or more of the guide depressions 54. The guide depressions 54 can be formed with a dimension operable to guide ME instruments for MER or other appropriate instruments.

Multiple guide depressions 54 can cooperate to form an enclosed or substantially enclosed guide area or passage 56. The guide area 56 defined by the guide depressions 54 define a second set of axes C, including axes Ca-Ce. The axes C can be substantially coaxial with axes B of the guide bores 52 formed in the guide section 22. As discussed above, the sliding section 32 allows the guide members 30 to move relative to the guide fixture 16. Therefore, the guide members 30 can be moved along axes A to position the guide members 30 near one another. This can allow the guide depressions 54 to cooperate to define a relatively small guide area 56 having a first dimension or shape. The guide bores 52 can have a second dimension or shape. The guide members 30 can also be moved apart so that the guide area 56 in no longer effectively formed.

The guide area 56 can include any appropriate shape or size. For example, the guide area can be substantially circular or annular. Similarly, the guide area 56 can be polygonal, multi-sided, etc. Also, the guide area 56 can be provided in any appropriate size. Also, the guide area 56 can be of the same or different shape than the guide bores 52.

In addition, the guide areas 56 can be provided or formed in any appropriate number. Forming five guide areas 56 is merely exemplary, as illustrated in FIG. 5. It will be understood that any appropriate number of guide depressions 54 can be formed in the guide members 30 to form any appropriate number of the guide areas 56. In addition, a kit of the guide members 30 can be provided for a selected procedure so that either intra- or pre-operatively a user can select the appropriate guide members 30 to create a selected number of the guide areas 56. The selected kit can allow for the creation of a different number, size, shape, etc. of the guide areas 56.

In addition, multiple sets of the guide members 30 can include varying numbers, sizes, shapes, etc. of the depressions 54. The different depressions can cooperated to form different guide areas 56. Thus, one skied in the art will understand, the user can select the appropriate set or group of the guide members 30 to create or form appropriate guide areas 56.

The drive system 10 can drive multiple instruments, such as a first instrument 60. The first instrument 60 can be passed through the drive section 12 to be guided with the guide fixture 16. The drive section 12 can include a holding section 12a that defines a plurality of passages there through that also define a drive axis E. The drive axis E can be aligned with a center axis or parallel to the guide area axes C or guide bore axes B.

The drive system 10 can include the drive or locomotion structure 11 and a drive motor 11a. The drive system 10 can be manual or electronically operated to drive the first instrument 60. The first instruments 60, which are driven through the guide fixture 16, can be guided with the guide members 30. As discussed further herein, a second instrument 62 can be driven with the drive portion 12 through the guide bores 52 defined by the guide section 22. The guide areas 56, defined by the guide members 30, can be provided substantially coaxial with the guide bores in the guide section 22. Although, it will be understood that each of the guide areas 56 can be aligned with at least one of the guide bores 52.

As illustrated in FIG. 5, the first instrument 60 can be guided through the guide area 56 defined by one or more of the depressions 54 in the guide members 30. The first instrument 60 can include any appropriate instrument, such as a ME. The ME can be provided in any appropriate diameter, such as about 0.7 millimeters, which can also include the diameter of an insertion cannula. It will be understood that the first instrument 60 can include any dimension, such as a diameter of about 0.1 mm to about 1 cm, or any shape. The guide area 56, defined by the guide depressions 54, can provide an appropriate dimension to allow for guiding of the insertion cannula 60 or just the ME alone.

The first instrument 60 passes the guide members 30 and through the guide section 22. The first instrument 60 can pass along axes B and axes C through the guide area 56 and the guide bores 52. The first instrument 60 can be so guided because it includes a dimension less than the dimension of the guide bore 52. If will be understood, however, that the guide fixture 16 can be inverted so that the first instrument has a dimension that is equal to the guide bores 52 and the guide members 30 are provided to as to not define the guide areas 56.

Also, as illustrated herein, a plurality of the first instruments can be guided with the guide fixture 16. For example, an array of five of the first instruments 60 can be guided with the guide fixture 16 along axes B and C. The first instruments 60 can be positioned relative to one another and can be guided through the guide fixture 16.

Figure 7:
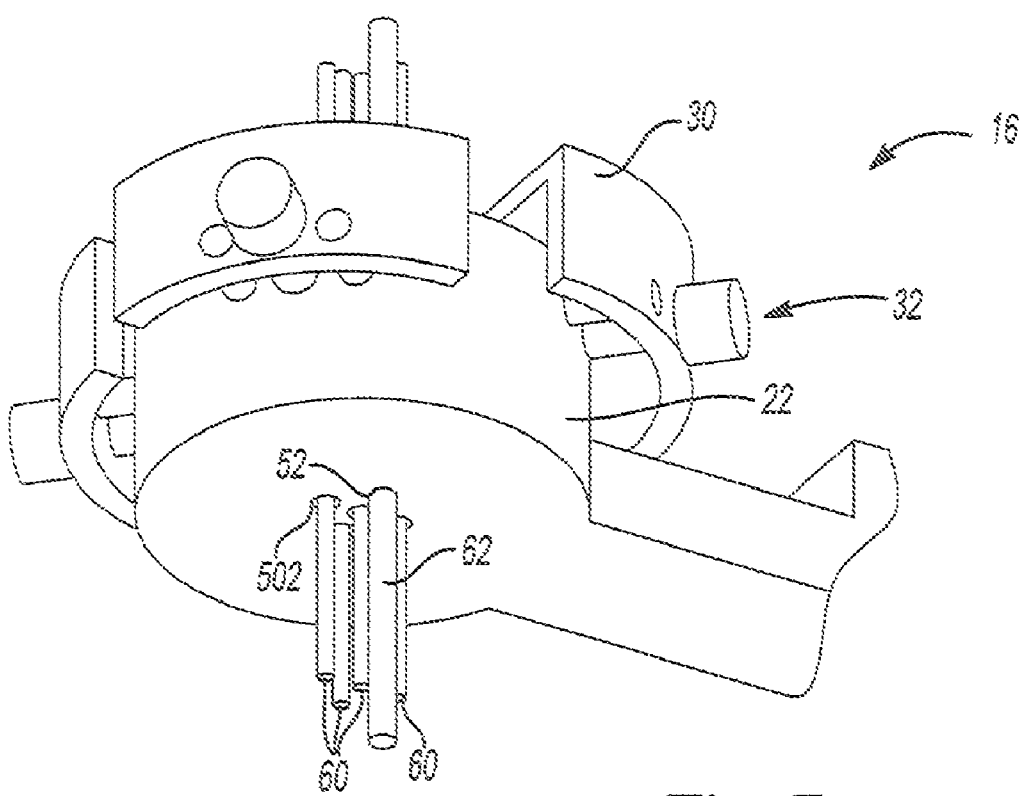
FIG. 7 is a perspective view of a guide fixture guiding two different instruments, according to various embodiments.

With reference to FIGS. 6 and 7, the guide members 30 can be oriented, such as moved along the axes A with the sliding sections 32, to allow opening of the guide areas 56 defined by the depressions 54 of the guide members 30. By moving the guide members 30 apart from one another, the guide members 30 may no longer guide the first instrument 60. Moving the guiding members along axes A can move them transverse to the longitudinal axis of the instrument or axis E of the drive section 12. The transverse movement can be perpendicular, substantially perpendicular, or at any angle to the axes (e.g. 30°, 45°, 60°, etc.).

As discussed further herein, and illustrated particularly in FIG. 6, one of the first instruments 60 can be removed from the guide section 22 at a selected time. With additional reference to FIG. 7, a second instrument 62 can be guided with the guide bore 52 when the guide members 30 are moved apart. The guide bore 52 can be dimensioned or the instrument 62 can be selected to include an appropriate dimension to be guided appropriately with the guide bore 52. The second instrument 62 can be any appropriate instrument, such as a DBS probe or lead. The second instrument 62 can be provided after a selected procedure is performed with the first instrument 60, or for any appropriate purpose.

The provision of multiple of the first instruments 60 can allow for the removal of one of the instruments 60 while the remaining first instruments 60 are positioned relative to the guide fixture 16 and the anatomy. The multiple first instruments 60 positioned into the anatomy can assist with reducing shift of portions of the anatomy, such as the brain, relative to the guide fixture 16. Thus, when the second instrument 62 is passed along the trajectory which is the same or similar to the selected first instrument 60 that is removed, the second instrument 62 can move to a position that was previously occupied by the removed first instrument.

The axes C of the guide area 56 can be provided in a substantially coaxial or parallel relationship to the axes B of the guide bores 52. This allows the first instrument 60, as illustrated in FIGS. 5-7, to pass through the guide area 56 and through a respective one of the guide bores 52. Further, when the guide members 30 are moved apart, the second instrument 62 can be guided with the guide bore 52 from which one of the first instruments 60 has been removed.

Because the guide area 56 is provided substantially coaxial or aligned with an axes B of the guide bore 52, the second instrument 62 can be moved along a substantially similar or identical path or trajectory as the first instrument 60. Therefore, a two-step procedure, for each set of the guide members 30, or two separate procedures can be performed substantially along the same axis or path. The substantially identical position of the guide fixture 16 can guide two different instruments with separate guide parts, including the guide area 56 and the guide bore 52. The instruments can have different sizes and shapes.

The guide members 30, each of which define at least one of the guide depressions 54, can define at least a portion of the guide area 56. The guide area 56 can define the axes C, as illustrated in FIG. 1. The axes C, of the guide area 56, can be substantially coaxial with the axes B of a respective one of the guide bores 52. In addition, according to various embodiments, each of the guide areas 56 can define an axes C that is parallel to each other and parallel to the guide axes B of the guide bores 52.

Providing the guide area 56 as being defined by more than one of the guide members 30 can allow for the formation and deformation of the specific guide areas 56. Therefore, as the guide member 30 moves toward the center of the guide section 22, the guide depressions 54 can be positioned relative to one another to define a guide area 56 and the axes C. When the guide members 30 are moved apart, the guide depressions can also be moved apart so that the guide area 56 is no longer specifically defined and an instrument, such as the second instrument 62, can pass through one of the guide bores 52. In other words, the guide members 30 can cooperate to define at least one of the guide areas 56 that can be positioned relative to one of the guide bores 52, such as coaxial therewith, to guide the first instrument 60. The guide members 30 can then be moved apart to allow the second instrument 62 to be guided with a respective one of the guide bores 52.

The drive system 10 can be interconnected or associated with a stereotactic head frame or support 70. The stereotactic head frame 70 can include various components that are interconnected with an anatomy 72. The stereotactic head frame 70 may be particularly interconnected with a head or cranial portion 74 of the anatomy. The stereotactic head frame 70 can be interconnected to the cranium 74 using various connection portions including fixation pins 76 that extend from connector or positioning arms 78. The positioning arms 78, which can be fixed to the cranium 74 with the fixation pin 76, can be interconnected with a positioning ring 80 at a second end. The positioning ring 80 can include areas to interconnect a plurality of the positioning arms 78 therewith.

Extending from the cranium 74 can be placement arms 82. The placement arms 82 can be interconnected with an arcuate track or placement track 84, via connecting arms 86. The placement arms 82 can be moved relative to the positioning ring 80, via a first connection mechanism 88. The placement arms 82 can be positioned relative to the placement track 84, via a second connection mechanism 90. The placement track 84 can also be moveably connected to the extension arms 86 in any appropriate manner. Therefore, the positioning ring 80 can be fixed to the cranium 74 and the placement track 84 can be positioned relative to the cranium 74 using the plurality of connection mechanisms 88, 90 and any other appropriate connection mechanism.

A truck or slide 92 can be moved along the placement track 84 to achieve a selected placement of the slide 92. As illustrated, the placement track 84 can include calibrated marks for determining a position of the slide 92 relative to the placement track 84. The connecting arms 86 can also include calibrated marking 96. The use of the stereotactic head frame 70 is generally known by one skilled in the art. For example, the head frame 70 can include a stereotactic head frame, such as the Leksell Stereotactic System® provided by Elekta AB.

The stereotactic head frame 70 can be positioned using navigation systems, such as the navigation systems discussed further herein and in U.S. patent application Ser. No. 10/651, 267 (now U.S. App. Pub. No. 2005/0049486), entitled "Method and Apparatus for Performing Stereotactic Surgery," incorporated herein by reference. Various tracking sensors can be interconnected with the stereotactic head frame 70 such as a first tracking sensor 98 positioned on the positioning ring, a second tracking sensor 100 positioned on the second connection 90, a third tracking sensor 102 positioned on the placement track 84, and a fourth tracking sensor 104 positioned on the slide 92 or the drive mechanism 10. The various tracking sensors 98-104 can be used with the navigation or tracking system to determine a position of each of the components of the stereotactic head frame 70 to determine a position of the slide 92 or the drive system 10 relative to the cranium 74. It will be understood, however, that any appropriate stereotactic head frame, either navigated or not, can be used with the drive system 10. In addition the various tracking sensors 98-104 can be any appropriate type or be used with any appropriate system, such as optical electromagnetic, acoustic, accelerometer, etc.

The instruments 60, 62 can also include tracking devices incorporated therewith. For example, the instruments can include tracking instruments integrated into the distal portions of the instruments, such as those disclosed in U.S. patent application Ser. No. 11/241,837 (now U.S. Pat. App. Pub. No. 2006/0084867), filed on Sep. 30, 2005, entitled "METHOD AND APPARATUS FOR SURGICAL NAVIGATION," incorporated herein by reference. These tracking devices can include one or more coils than can work with an electromagnetic tracking system. In addition, or alternatively, optical or other tracking devices can be associated with the instruments 60, 62. Also, the instruments can be tracked or navigated based upon a tracked position of the drive system 10 and known drive depth of the instruments 60, 62. In this case the trajectory can be determined based upon the orientation of the drive system or the head frame. Each of the guide members 30 can also include similar tracking devices to track the location of the guide members 30 and the respective guide depressions 54.

The drive system 10 can be interconnected with the slide 92 so that it can be moved relative to the cranium 74 of the patient 72. The stereotactic head frame 70 can be used to position the slide 92 relative to the patient 74 in any appropriate manner. As one skilled in the art will understand, the slide 92 can be positioned relative to the cranium 74 in a substantially planned manner or selected manner so that when driving the instruments 60, 62 into the cranium 74 the instruments 60, 62 proceed along a selected path. The selected path can ensure the positioning of the instruments 60, 62 in a selected position within the cranium 74. As one skilled in the art will further understand, the path or trajectory of the instruments 60, 62 can be selected based upon a selected final position of the instrument 60, 62 within a brain 106 of the patient 72.

According to various embodiments, the drive system 10 can be interconnected to a smaller or small-scale head frame or support mechanism 120, as illustrated herein. The small-scale head frame mechanism 120 can be any appropriate mechanism, such as the NEXFRAME™ sold by Image Guided Neurologies of Florida, USA or Medtronic, Inc. of Minnesota, USA. The small-scale head frame 120 can include the drive system 10 interconnected therewith. Also, movement of the drive system 10 can be allowed relative to the cranium 74 to ensure an appropriate or selected position of the drive system 10 relative to the cranium 74.

The small-scale head frame 120 can include a base 122 that is fixedly connected to the cranium 74 of the patient 72. The base 120 can define an aperture or opening 124 that allows the instruments 60, 62 to pass through the base 120 into the cranium 74. A moveable base 126 can be interconnected to the base 122 and the drive system 10 can be connected to the moveable base 126. Various set or locking screws 128 can be used to fix the moveable base 126 to a selected position. Further, various markings can be provided on the moveable base 126 or the fixed base 122 to assist in obtaining a selected orientation of the moveable base 126 to the cranium 72.

Further, various tracking sensors can be interconnected with the small-scale head frame 120. For example, a fifth tracking sensor 130 can be interconnected with the fixed base 122. A sixth sensor 132 can be interconnected with the moveable base 126. The sixth sensor 132 can also be used to determine the position of the moveable base relative to the fixed base 122 and the cranium 74. Again, the fourth sensor 104 can be interconnected with the drive system 10 to determine a position of the drive system 10 relative to the small-scale head frame 120. The various tracking sensors can be used with a tracking and navigation system to determine a position of the various components of the small-scale head frame 120 or the drive system 10 relative the cranium 74 and the brain 106, as further discussed herein.

The various components of the drive system 10 and the stereotactic head frame 70 or the small-scale head frame 120 can be provided to allow for efficient sterilization or sterile use. The guide members 30 can be removed from the slide portions 32 to allow the guide fixture 16 and the guide members 30 to be sterilized in an appropriate manner. The removal of the guide members 30 from the guide fixture 16 can allow for minimal small areas for sterilization and increase the effectiveness of sterilization.

The stereotactic head frame 70 can be formed of sterilizable materials. The stereotactic head frame 70, therefore, can be removed after a procedure, cleaned and sterilized for additional procedures. The stereotactic head frame 70 can also be formed of a single use material, either a metal, ceramics, or polymers, but are not limiting to the present teachings. Also, the small-scale head frame 120 can be formed of a rigid polymer to provide for a substantial single use device. Alternatively, the small-scale head frame 120 can be formed of a metal, metal alloy, ceramics, or polymers, but are not limiting to the present teachings, that can also be used for multiple procedures.

Figure 10:
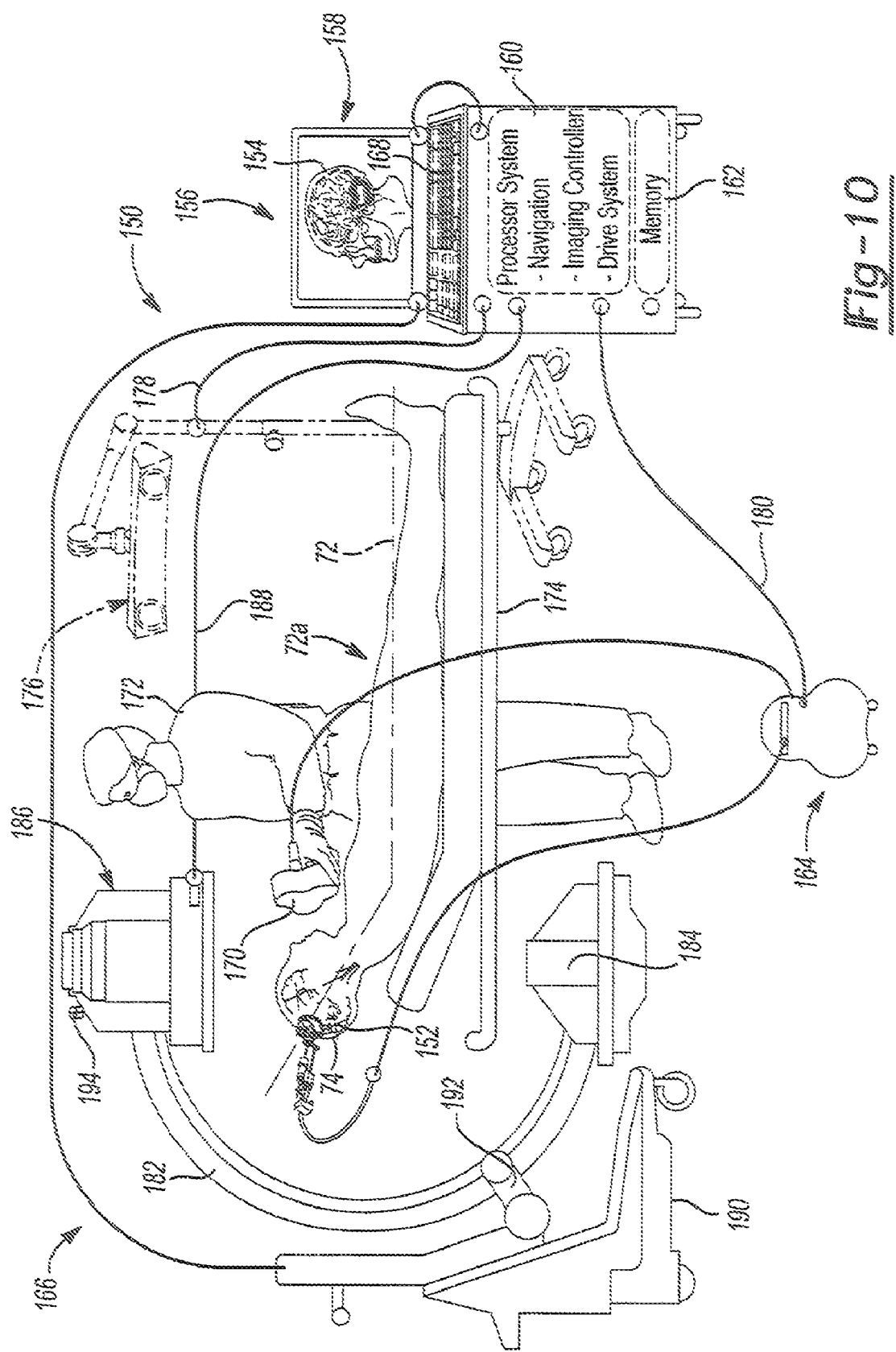
FIG. 10 is an environmental view of a surgical navigation system including a drive system and guide fixture according to various embodiments.

The drive system 10 and the guide fixture 16 can be used in an operating theater, including a surgical navigation system 150, with reference to FIG. 10. Various surgical navigation systems include those described in U.S. patent application Ser. No. 10/651,267 (now U.S. Pat. App. Pub No. 2005/0049486), filed on Aug. 28, 2003, incorporated herein by reference. The surgical navigation system 150 can include an image based system, an imageless system, an atlas or diagram based system, or combinations thereof. One skilled in the art will understand that the surgical navigation system 150 can require the registration of the patient 72, which defines patient space, to a tracking system, discussed further herein. According to various embodiments, registration can include registration between image space, defined by image data or atlas data, and the patient space.

The patient space is generally defined as the area in which an instrument is to be navigated relative to the patient 72. The registration of the patient space to other space allows for a correlation of a tracked position of an instrument, such as the instruments 60, 62 or other portions, such as the stereotactic head frame 70 or small-scale head frame 120, to a different reference frame. Registration is generally understood by one skilled in the art and can include identifying a fiducial or plurality of fiducials 152 on the patient 72 and finding similar points in an image data 154. The fiducials 152 marked as X's on the patient 72 are merely exemplary, and can include artificial fiducial points or natural or anatomical fiducial points.

The navigation system 150 can generally include a workstation 156 that can include a display device 158 associated with a processor system 160. The workstation 156 can also include a memory system 162. The processor system 160 can be interconnected with various other portions in the surgical navigation system, including a tracking device 164, an imaging device 166, or other appropriate portions. The workstation 156 can also include a user input system, such as a keyboard 168. The user input can also include a foot pedal, a mouse, a touch screen, or any other appropriate user input system. The user can input instruments or commands into the work station 156 to select or track instruments within the surgical navigation system 150.

The surgical navigation system 150 can also include the tracking system 164, which can exemplarily include an electromagnetic tracking system. The electromagnetic tracking system 164 can include an electromagnetic localizer 170. According to the various embodiments the electromagnetic localizer 170 can be held by a user 172, such as a surgeon. If will be understood, that the electromagnetic localizer 170 can also be provided in a fixed position relative to the patient 72, such as associated with a surgical couch or bed 174. The electromagnetic tracking system 164 can be associated with the work station 156 via a separate transmission line 180.

According to various embodiments, the tracking system can include an optical tracking system. The optical tracking system can include an optical localizer 176. The optical localizer 176 can be interconnected with the work station 156 via a transmission line 178. It will be understood that the transmission lines 178, 180 can be wireless or wired, depending up the selected system. It will also be understood that any appropriate tracking system can be used, such as sonar, acoustic, accelerometer, laser, radar, etc.

The surgical navigation system 150 can also include the imaging device 166. The imaging device 166 can exemplary include an x-ray fluoroscopic device, such as a C-arm 182. The C-arm 182 can include an x-ray source 184 and an x-ray receiver or intensifier 186. An image or image data can be created and transferred, via a transmission line 188 to the work station 156. The image data created with the imaging device 166 can be displayed on the display device 158 as the image data 154 or can be displayed relative to previously acquired image data on the display device 158. Generally the C-arm 182 can be supported by a floor unit 190 and moved about a mechanical axis 192. The C-arm 182 can be controlled by the processor system 160 or can include a separate control system for the C-arm 182.

It will be understood, however, that the imaging device 166 can include any appropriate imaging device. For example, imaging device 166 can include a Fluoroscopic O-arm™ imaging devices (i.e. devices sold by Breakaway Imaging, LLC. having a place of business in Massachusetts, USA), a magnetic resonance imaging system, such as the PoleStar® magnetic resonance imaging system provided by Medtronic, Inc., a positron emission tomography (PET) imaging system, a computer aided tomography (CAT) imaging system, a SPECT imaging system, or any appropriate imaging system. The imaging device 166 can be provided in the operating theater to obtain or create intra-operative image data. It will be understood that previously acquired image data can be provided for viewing on the display device 158, such as after being stored in memory system 162.

The imaging device, such as the C-arm 182, however, can be provided in the room where the procedure occurs to be operated by the user 172. Operation of the C-arm 182 is understood by one skied in the art, and can be similar to the ARCADIS® Orbic or ARCADIS® Orbic 3D from Siemens Medical of Germany.

As discussed above, each of the drive system 10, the head frame 70, and the small-scale head frame 120 can include tracking sensors. In addition, the imaging system 166 can include a tracking sensor 194 so that the position of the imaging system 166 relative to the patient 72 can be determined. An axis 72a of the patient 72 can include a longitudinal axis of the patient 72. The axis 72a of the patient can also assist in displaying or orienting various portions relative to the patient.

The image data 154 of the patient 72 can be displayed on the display device 158. Various icons, representing the instruments 60, 62 can be superimposed on the image data 154 for display on the display device 158. The icons can be used by the user 172 to ensure or confirm the appropriate position, trajectory, path, and the like of the instruments 60, 62 into the patient 72. The various tracking sensors can be tracked by the appropriate tracking systems 164, 176 and icons representing locations of tracked portions can be displayed on the display device 158. The navigation processor, which can be a part of the processor system 160, can be used to determine the tracked position of the instruments 60, 62 for display relative to the image data 154.

According to various embodiments, the imaging device 166 can be used to confirm an absolute or selected position of the instruments 60, 62 in the patient 72. For example, the instruments 60, 62 can be driven into the patient 72 and an image can be obtained of the position of the instruments 60, 62 within the patient with the imaging device 166. The image data can be displayed on the display device 158, which can include both image data of the patient 72 and actual image data of the position of the instruments 60, 62.

Figure 11:
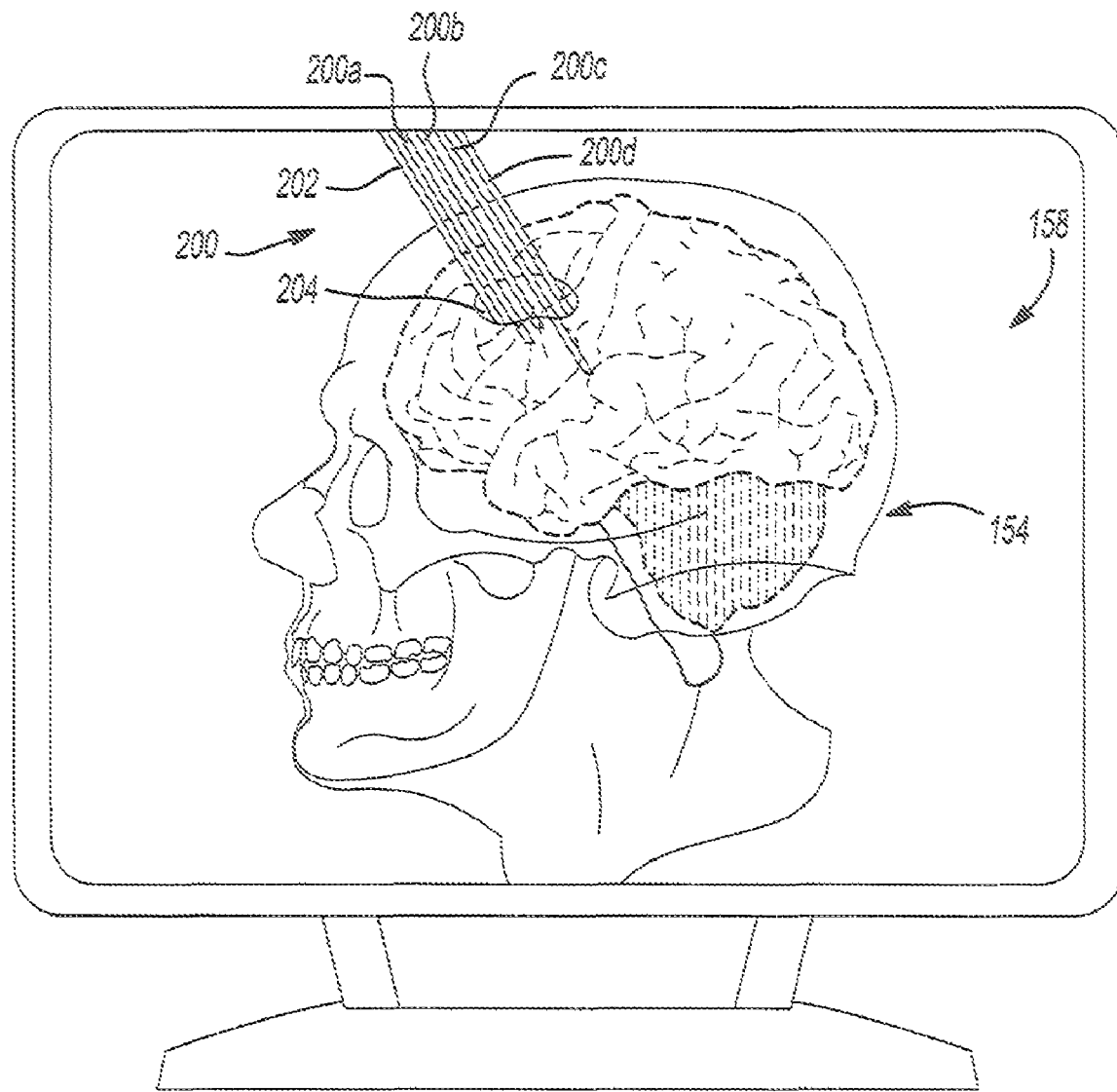
FIG. 11 is a detailed view of a display device according to various embodiments.

With reference to FIG. 11 the image data 154 displayed on the display device 158 can include an icon 200 or plurality of icons 200a, 200b, 200c and 200d. The icons 200 can represent a position of the first instruments 60 relative to the patient 72. A second icon 202 can also be illustrated relative to the image data 154. The second icon 202 can represent a position of the second instrument 62 relative to the first instruments 60.

The icons 200, 202 can be displayed relative to the image data 154 based on various information. For example, the icons 200 can be based upon a tracked position of the first instrument 60 relative to the patient 72. The tracked position can include a determined or tracked position of the first instrument 60 directly, a known trajectory and movement length of the instrument 60 relative to the tracked position of the drive system 10, or image data directly of the instruments 60, 62 within the patient 72.

A target area 204 in the anatomy can be preselected or determined, as discussed further herein, and displayed relative to the image data 154. According to various embodiments, the first instrument 60 can include ME. The ME can be used to record or determine various activities within the brain 106 of the patient 72. Although the target region 204 can be based upon preacquired image data of the patient 72, the ME 60 can be used to verify or confirm the selected target.

The ME 60 can be maintained within the patient 72, via the guide fixture 16, while the second instrument 62 can be moved and axially guided with the guide fixture 16 as well. The second icon 202 can illustrate the position of the second instrument 62 relative to the target region 204. The first instruments 60 can help hold the brain in position relative to the guide fixture 16 while the second instrument is moved into the selected or recorded position.

Figure 12:
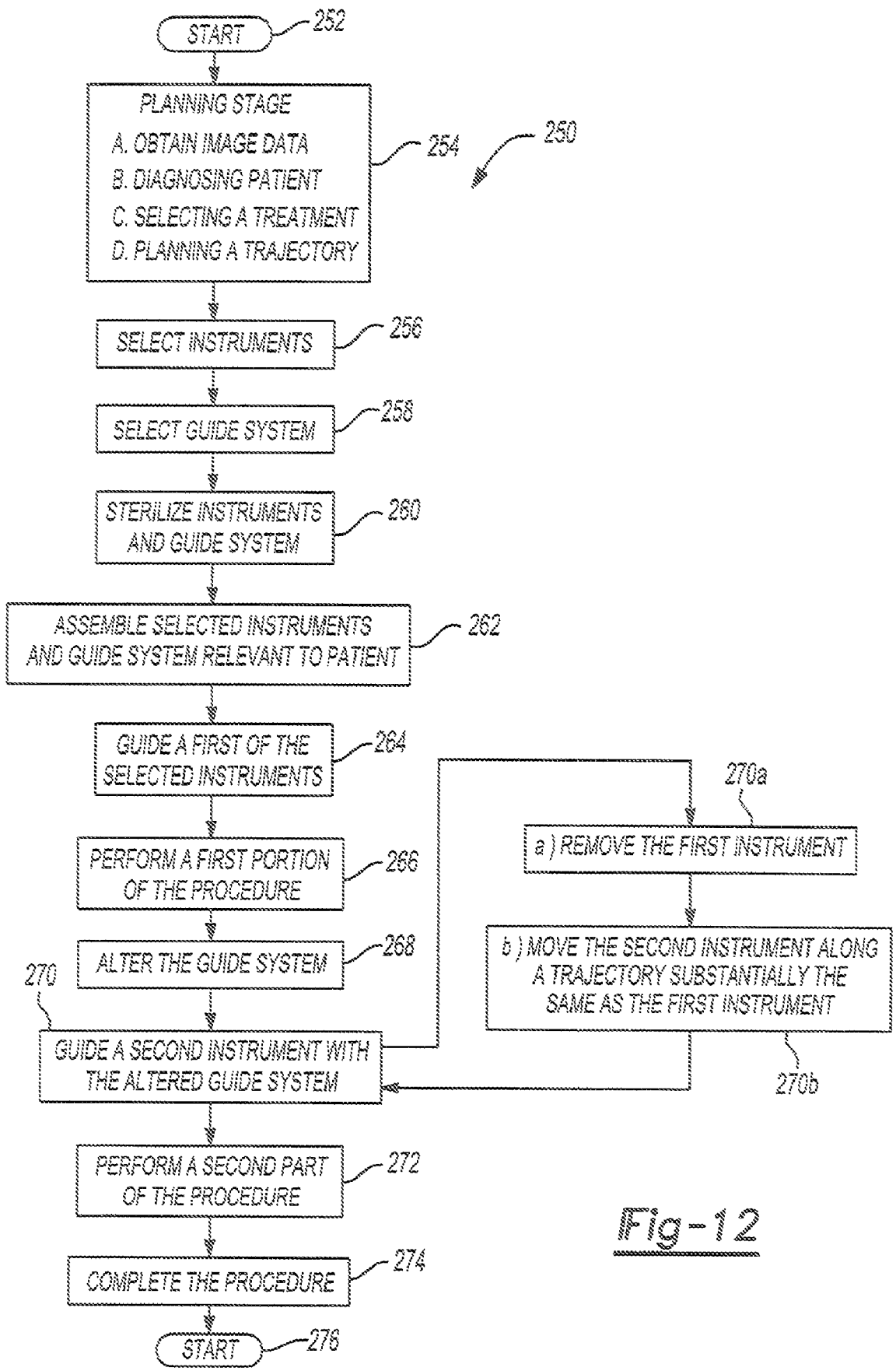
FIG. 12 is a flow diagram of a method according to various embodiments.

With reference to FIG. 12, and the previous FIGS. 1-11 as noted herein, a method 250 and system can be provided for applying a therapy to the patient 72. The method 250 can be used in conjunction with the various instruments 60, 62 and other apparatuses, such as the drive system 10, discussed above. The method 250, it will be understood by one skilled in the art, is merely exemplary of a process or method of using the system described above. Further, the method 250 is exemplarily illustrated and discussed in relation to moving the instruments 60, 62 relative to the cranium 74 and the brain 106. One skilled in the art will understand, the various systems described above can be used to move the instrument relative to any appropriate portion of the anatomy.

The method 250 can begin in block 252. The method 250 can then progress to a planning stage 254. The planning stage 254 can include various procedures and steps. For example, the planning stage 254 can include obtaining image data, diagnosing the patient, selecting a treatment, planning a trajectory, or other appropriate portions.

One skilled in the art will understand that the planning stage 254 can include any appropriate portions. For example, the user can diagnose the patient. The diagnosis can include any appropriate diagnoses, and discussion herein regarding the diagnosis and treatment options of stimulating a selected region of the brain 106 is merely exemplary. For example, the diagnosis can include epilepsy, a brain tumor, or any other appropriate diagnosis.

The planning stage of block 254 can also include obtaining image data. The image data obtained of the patient can include any appropriate image data, such as MRI image data, PET image data, computer aided tomography image data, x-ray image data, or the like. The image data can be of the patient to assist in the diagnoses of the patient or in the planning of a trajectory. The image data of the patient can be used during the surgical procedure, as discussed above, or can be used for diagnosis the patient alone. Nevertheless, the image data can assist the user in performing a procedure or diagnosing the patient and planning the selected trajectory and treatment of the patient.

The planning stage in block 254 can include selecting a treatment for the patient 72. The treatment for the patient can be any appropriate treatment, such as a biopsy, a stimulation, an ablation, or any appropriate treatment. The treatment of the patient 72 can be selected based upon the diagnosis of the patient and the image data obtained of the patient. The treatment, which can include the placement of a deep brain stimulation probe, can be performed according to various generally known techniques.

The planning stage 254 can also include planning a trajectory. The planning of the trajectory can include planning a path for an instrument, planning an insertion point for an instrument, and other appropriate trajectory procedures. The planning of the trajectory can include determining a most appropriate entry point and path to position a selected instrument, such as a DBS probe, within a selected portion of the patient.

It will be understood that the planning stage in block 254 can include any appropriate planning procedures. The exemplary planning procedures discussed above are provided merely for the current discussion and are not a limiting example. The planning stage 254 can encompass all appropriate procedures that can occur prior to performing a selected surgical procedure.

After the procedure is planned, instruments can be selected in block 256. The selection of instruments in block 265 can include a selection of various instruments, such as a ME and a DBS. The selection of the instruments in block 256 can also include the selection of instruments according to various sizes. For example, the ME instrument can be selected to include a diameter of about 0.7 millimeters or less, a selected shape, or configuration. The ME selection can also include selecting a cannula of an appropriate size, which can include a maximum diameter of about 0.7 millimeters and the ME including a diameter less than about 0.7 millimeters. The ME can be selected to include a pickup or recording radius of about 5 to about 1000 micrometers, including 200 micrometers from a selected point on the ME, which can be illustrated relative to the target 210 on the display device 158.

The selection of instruments in block 256 can also include the selection of an appropriate DBS probe. The DBS probe can include any appropriate diameter, such as about 1.3 millimeters. It will be understood that the deep brain stimulation probe can also include a stimulation radius of about 500 to about 5000 micrometers, including 2500 micrometers from a selected point. The DBS probe can be selected of any appropriate size and the 1.3 millimeter deep brain stimulation probe is merely exemplary.

Other instruments can also be selected and can include an ablation catheter, a biopsy needle or cannula, a therapy delivery device (e.g. a cannula), or any appropriate instrument. The instruments can also be chosen to achieve a selected procedure such as delivery of a pharmaceutical, radio active seed, pharmaceutical seed, etc. The instruments discussed herein are merely exemplary and described for clarity of the current discussion.

The instruments selected in block 256, however, can include varying dimensions. The varying dimensions of the instruments selected in block 256 can include diameters, perimeter dimensions, or any other appropriate dimensional differences. Further, the instruments selected in block 256 can include multiple perimeter shapes. For example, the instruments selected in block 256 can be substantially cylindrical, include an annular perimeter, a polygonal perimeter, or any other appropriate perimeter shape. Therefore, the instrument selected in block 256 can be of multiple sizes, but can be moved or used in a single procedure relative to a single portion of the anatomy, such as the brain 106.

The selection of the instruments can be based upon or influence the selection of a guide system in block 258. The selection of the guide system in block 258 can include the selection of various portions, including those discussed above. For example, the guide system can include a selection of a guide support, including the stereotactic head frame 70 or the small-scale head frame 120. Further, the selection of the guide system can include the selection of the drive system 10. The selection of the guide system can be selected based upon the instrument selected in block 256.

The instruments and the guide system can be optionally sterilized in block 260, or otherwise prepared for the procedure. As discussed above, the instruments selected in block 256 and the guide system selected in block 258 can be provided as a substantially single use or a disposable system that is provided sterilized for a procedure. Therefore, sterilizing the instruments and guide system in block 260 is optional depending upon the selected instrument and guide system. According to various embodiments, the guide members 30 can be removed from the guide fixture 16 to allow for the minimization of small crevices or areas in the guide fixture 16. The dimensions of the guide members 30 can allow for maintenance and identification of the guide members 30 during and after the sterilization process.

Once the instruments are prepared for the procedure, such as via the optional sterilization in block 260, the selected instruments and guide system can be assembled relative to the patient in block 262. The assembly of the instruments and guide system can include any appropriate steps. For example, the drive system can be assembled so that the guide fixture 16 is positioned relative to the drive portion of the drive system 10.

Further, the guide members 30 can be assembled on to the slide sections 32, as illustrated in FIGS. 1-2. The assembly of the guide members 30 on the guide fixture 16 can include positioning the guide members 30 so that they are moveable relative to the guide section 22. The positioning of the guide members 30 relative to the guide fixture 16 can include assembling various portions of the slide section 32, such as the third slide member 38.

The assembly of the guide system can include the determination of the appropriate guide members 30. The appropriate guide members 30 can ensure that an appropriate guide area 56 and appropriate number of guide areas can be defined or formed relative to the guide section 22. As discussed above, the guide area 56 can be defined with the guide depressions 54 to guide the selected instrument, such as an ME. The guide members 30 can be moved to a second position to allow the guide bores 52 to guide a second instrument, such as the DBS probe.

The assembly of the instruments and guide system can also include the positioning of the appropriate frame or support relative to the patient 72. For example, the stereotactic head frame 70 or the small-scale head frame 120 can be positioned relative to the patient 72. The drive system 10 can then be interconnected to the support assembly. The support system and drive system can then be moved relative to the patient, with or without the navigation system 150. According to various embodiments, a robotic system can also be used to position the drive system 10 relative to the patient 72. Using appropriate information, such as information from the navigation system 50, a robotic system can be programmed or directed to move the drive system 10 relative to the patient 72.

Once the instruments and guide system have been assembled relative to the patient, a first instrument can be guided in block 264. The guiding of the first instrument in block 264 can be performed when the guide members 30 are positioned in a first position, as illustrated in FIG. 5. As illustrated in FIG. 5 the guide members 30 can be positioned substantially dose to one another or near a close point. At the close point, the guide depressions 54 define the guide area 56 and the axes C.

Guiding the first selected instrument can include guiding a plurality of first selected instruments. For example, as illustrated in FIG. 5, five of the first instruments 60 can be driven info the patient 72 in a selected array. The locomotion portion 11 can be operated, manually or powered, to move the drive section 12*a* that holds the instruments. For example, five ME can be driven or guided into the brain 106 of the patient 72 for performing a selected portion of a procedure. The ME can be driven into the patient in any appropriate manner, such as within a grid or perimeter that can include any appropriate dimensions. For example, the five ME can define an array between one millimeter and twenty millimeters on a side. Further, the ME could be provided at a selected distance from one another on center, such as about one millimeter to about five millimeters. Also, the first instruments can be driven and guided to different depths, as illustrated in FIG. 11. It will be understood that any appropriate number of instruments can be guided when guiding a first instrument in block 264. Further, the guide members 30 can be provided in any appropriate number, or any appropriate number of the guide members 30 can be moved to an appropriate location to guide the selected number of instruments.

The guiding of the first instrument in block 264 can also include navigation guidance or moving the instrument relative to the patient. As discussed above, the first instrument can include a ME that is driven into the brain 106 of the patient 72. The ME can be guided with the navigation system 50, according to generally known techniques. For example, a tracking sensor can be interconnected with the ME and the position of the ME can be tracked relative to the image data 154 for display on the display device 156, as illustrated in FIG. 10.

The ME, or any appropriate instrument, can also be guided by determining an amount of movement and a known trajectory of the guide or drive system 10.

Once the first instrument is guided in block 264, a first portion of the procedure can be performed in block 266. The procedure performed in block 266 can include any appropriate portion of the procedure, such as recording the information with the ME. Therefore, performing the procedure in block 266 can also include the recording of the information as the ME is moved relative to patient 72.

After the first portion of the procedure is performed in block 266, the guide system can be altered in block 268. The guide system can be altered by moving the guide members 30. According to various embodiments, the guide members 30 can be slid further from one another along axes A to disassociate the guide members 30 and remove the guide area 54. This allows for guiding of the second instrument with only the guide bore 52. The altering of the guide system, such as moving the guide members 30, in block 268, can allow guiding of the second instrument with the substantially same guide system and along a substantially similar trajectory as the first instrument. As discussed above, the axes C of the guide area 56 and the axes B of the guide bore 52 can be substantially aligned or coaxial. Thus, the second instrument can reach the same position as the first instrument, even though the second instrument includes a dimension to be guided with the guide bore 52 alone.

The second instrument can be guided in block 270. The guiding of the second instrument in block 270 can include at least removing the first instrument or one of a plurality of the first instrument in block 270*a*. The second instrument can then be moved along a trajectory similar to or substantially identical to a trajectory of the first instrument in block 270*b*. Removing the first instrument in block 270*a* can open up or allow access to the guide bore 52 that is substantially coaxial with the previously created guide area 56. The guide bore, according the various embodiments, can include a larger dimension than the guide area 56. Therefore, the second instrument, such as the DBS probe, can be guided with the guide bore 52 after moving the guide members 30.

The guide bore 52 can be provided substantially coaxial with the guide area 56, therefore, the second instrument can be provide or guided along a substantially identical trajectory or axis as the first instrument. This can allow the second instrument to be provided in a substantially identical location as the first instrument. Further, the movement of the guide members 30, when altering the guide system in block 268, allows for an efficient provision of the second instrument in a substantially identical trajectory of the first instrument. The guide members 30 can be provided to move in a substantially efficient manner to allow efficient access to a second coaxial guide portion, such as the guide bore 52.

The second instrument guided in block 270 can be guided in a substantially similar manner to the first instrument. Therefore, one skilled in the art will understand that the second guided instrument can be navigated with the navigation system 150, can be moved a selected distance along the determined or guided trajectory, or guided in any appropriate manner.

A second portion of the procedure can be performed in block 272. As discussed above, the second portion the procedure can include stimulation of the brain 106 with the DBS probe. The stimulation of the brain 106 can be any appropriate stimulation, such as temporary stimulation or implantation of the DBS probe for a permanent stimulation system. Further, as discussed above, the selected procedure is merely exemplary and provided for the current discussion. Therefore the first and second portion of the procedure can include any appropriate procedure.

According to various embodiments, the first portion of the procedure can include recording activity in the brain 106, a spinal column, or any other appropriate area. Performing the second portion of the procedure can include ablation of the selected portion of the anatomy, delivery of a therapy (e.g. chemical delivery, radioactive seed delivery, or the like), or movement of a biopsy needle or cannula relative to the selected portion of the anatomy.

The procedure can be completed in block 274, which can include various portions. Completing the procedure can include closing an access portal to the interior of the patient 72, removing instruments, fixing implants or prosthesis relative to the patient 72, or any other appropriate portions. Then the method or procedure can end in block 276.

The method 250 can be used to guide two or more instruments relative to the patient 72 in any appropriate manner. As discussed above, the instruments can include substantially different dimensions or shapes, but can be selectively guided along a substantially identical trajectory with the guide system. Further, the instruments can be guided into the patient 72 in any appropriate manner. For example, the first guided instrument can be smaller in dimension than the second instrument or vice versa. Thus, the guide system, such as the guide fixture 16, can be used to guide more than one instrument along a substantially identical trajectory to perform two procedures or two parts of a single procedure along a substantially identical trajectory, in a substantially identical location within the patient, or other appropriate coaxial or aligned portions.

Guiding two instruments along the same path or trajectory can be done without removing or disassembling the guide portion 16. The guide members 30 can be moved relative to the annular wall 22*a*, but are not required to be removed from the guide fixture 16. Thus, the drive system 10 and the guide portion can be assembled in an appropriate manner for a procedure and the multiple instruments can be driven or delivered into the anatomy without disassembling the guide portion 16, but only altering the guide portion 16.

The description and teachings herein are merely exemplary in nature and, thus, variations that do not depart from the gist of the teachings are intended to be within the scope of the teachings. Such variations are not to be regarded as a departure from the spirit and scope of the teachings.

What is claimed is:

1. A method of guiding a first instrument and a second instrument relative to a selected portion of an anatomy, comprising:

providing a guide fixture with a guide section;

providing a plurality of guide members each defining a plurality of guide depressions;

moveably attaching the plurality of guide members to the guide section;

aligning the guide fixture with the selected portion of the anatomy;

forming a first guide configuration by moving the plurality of guide members from a first position to a second position relative to a fixed point of the guide fixture such that the plurality of guide depressions of each of the plurality of guide members cooperate with a sub-plurality of the plurality of guide depressions of at least another two of the plurality of guide members to form a plurality of first guide areas;

maneuvering the first instrument relative to the guide section and one of the plurality of first guide areas while the plurality of guide members are in the first guide configuration;

altering the first guide configuration to form a second guide configuration by moving at least one of the plurality of guide members relative to the guide section such that at least another one of the plurality of first guide areas is at least expanded while the one of the plurality of first guide areas remains unchanged; and maneuvering the second instrument relative to the at least one expanded first guide area of the second guide configuration.

2. The method of claim 1, wherein moving the guide members from a first position to a second position includes moving the guide members from a position distance away from the fixed point to a position close to the fixed point.

3. The method of claim 2, wherein moving the guide members includes moving the guide members along a radial axis defined by the guide fixture extending from the fixed point.

4. The method of claim 1, further comprising:
tracking a location of at least one of the first instrument, the second instrument, or combinations thereof relative to the anatomy.

5. The method of claim 1, further comprising:
determining a trajectory of maneuvering the first instrument; and
maneuvering the second instrument along the same trajectory.

6. The method of claim 1, further comprising:
the plurality of guide members each having a quadrant member that is defined by a span along an arc.

7. The method of claim 1, further comprising:
providing a sliding section extending radially from the guide fixture along an axis aligned through the fixed point; and
sliding the guide members along the sliding section.

8. The method of claim 1, further comprising:
performing a procedure on the selected portion of the anatomy.

9. The method of claim 8, wherein performing the procedure on the selected portion of the anatomy includes performing a biopsy, performing a micro electro recording, performing a deep brain stimulation, implanting a deep brain stimulation probe, moving a micro-electrode instrument to a selected position, positioning a radio active seed, moving a catheter instrument to a selected position, or combinations thereof.

10. There method of claim 1, wherein each of the plurality of first guide areas defines an axis;
and
wherein moving the plurality of the guide members from the first position to the second position includes moving the plurality of guide members transverse to the defined axes.

11. A method of guiding an instrument relative to a selected portion of an anatomy, comprising:
providing a drive system having a drive axis;
supporting the drive system on a support structure relative to the selected portion of the anatomy;
aligning the drive system with the selected portion of the anatomy;
providing a guide fixture with a plurality of guide members and a guide section, each of the plurality of guide members defining a plurality of separate guide depressions;
aligning the guide section with the drive axis;

moving the plurality of guide members into a first configuration such that the plurality of guide depressions of each of the plurality of guide members cooperate with a sub-plurality of the plurality of guide depressions of at least another two of the plurality of guide members to define a plurality of separate first guide areas, wherein the plurality of first guide areas partially occludes a corresponding plurality of second guide areas defined by the guide section and axially spaced apart from the plurality of guide members;

moving a sub-plurality of the plurality of guide members into a second configuration allowing unobstructed access to a corresponding sub-plurality of the plurality of second guide areas while maintaining another sub-plurality of the plurality of first guide areas unchanged; and maneuvering the instrument along the drive axis and through the guide section.

12. The method of claim 11, further comprising:
obtaining image data of the selected portion of the anatomy;
determining an area to be treated within the selected portion of the anatomy;
selecting an instrument to provide the treatment to the selected portion of the anatomy; and
determining a trajectory along which the instrument can be maneuvered to provide the selected treatment.

13. The method of claim 12, wherein aligning the drive system with the selected portion of the anatomy includes aligning the drive system with the determined trajectory.

14. The method of claim 11, further comprising:
providing a first instrument and providing a second instrument;
guiding the first instrument with one of the plurality of first guide areas that partially occludes a corresponding second guide area; and
guiding the second instrument with one of the corresponding sub-plurality of second guide areas.

15. The method of claim 11, wherein the plurality of first guide areas each define a first guide dimension smaller than a second guide dimension of the corresponding plurality of second guide areas.

16. The method of claim 14, wherein the first instrument and the second instrument are both guided along a substantially identical trajectory.

17. The method of claim 16, wherein maneuvering the instrument along the drive axis includes maneuvering the first instrument along the drive axis and maneuvering the second instrument along the drive axis.

18. The method of claim 17, further comprising:
driving the first instrument and the second instrument with a drive section of the drive system.

19. The method of claim 11, wherein moving the plurality of guide members into a first configuration further includes:
moving a first of the plurality of guide members and a second of the plurality of guide members to a substantially adjacent position; and
defining a perimeter of one of the plurality of first guide areas with a first depression of the plurality of guide depressions in the first guide member and a second depression of the plurality of guide depressions in the second guide member when the first and second guide members of the plurality of guide members are substantially adjacent to one another.

20. The method of claim 11, wherein the plurality of first guide areas and the corresponding plurality of second guide areas defined by the guide section of the guide fixture are substantially coaxial.

21. The method of claim 11, wherein moving the plurality of guide members into a second configuration includes turning a drive screw to interact with at least one of the plurality of guide members to move at least one of the plurality of guide members relative to the guide section.

22. The method of claim 11, further comprising:
providing a surgical navigation system including a tracking system having a tracking sensor associated with the instrument;
tracking the instrument with the tracking sensor; and
determining a position of the instrument relative to the selected portion of the anatomy.

23. The method of claim 22, further comprising:
obtaining image data of a selected portion of the anatomy;
superimposing an icon representing a position of the instrument relative to the obtained image data of the anatomy.

24. The method of claim 11, further comprising:
forming the plurality of first guide areas and the corresponding plurality of second guide areas substantially co-axially relative to a guide axis; and
wherein moving the plurality of guide members includes moving the plurality of guide members transverse to the guide axis.

25. A method of guiding an instrument relative to a selected portion of an anatomy, comprising:
providing a guide fixture including a guide section and a plurality of separately movable guide members associated therewith, each of the plurality of guide members having a plurality of guide depressions formed on a perimeter thereof;
moving the plurality of guide members to a first position relative to the guide section such that the plurality of guide depressions of each guide member cooperate with at least a sub-plurality of the plurality of guide depressions of another two of the plurality of guide members to define a plurality of first guide areas, wherein a perimeter of one of the plurality of first guide areas is formed by cooperation of one of the plurality of guide depressions from each of the plurality of guide members and at least a perimeter of another one of the plurality of first guide areas is formed by cooperation of another one of the plurality of depressions from only two adjacent guide members of the plurality of guide members;
guiding a plurality of first instruments along a plurality of co-linear first instrument axes and through the plurality of first guide areas;
moving a sub-plurality of the plurality of guide members transverse to the instrument axes to a second position;
removing one of the plurality of first instruments from one of the plurality of first guide areas that was associated with at least two of the moved sub-plurality of guide members; and
guiding a second instrument along a second instrument axis relative to an instrument axis associated with the one removed instrument of the plurality of first instruments.

26. The method of claim 25, wherein providing the guide fixture includes providing a substantially annular guide section defining a center;
wherein moving the plurality of guide members includes moving each of the plurality of guide members substantially along a respective plurality of radial axes defined by the guide section and originating from the center.

27. The method of claim 26, further comprising:
providing a slide section extending radially outward from the guide section;
wherein moving the plurality of guide members includes sliding the guide members along the slide section about the radial axis.

28. The method of claim 27, wherein guiding a second instrument includes guiding the second instrument through a guide bore defined in the guide section.

29. The method of claim 25, further comprising:
defining a plurality of guide bores within the guide section;
wherein each of the plurality of first guide areas has a first dimension; and
wherein each of the plurality of guide bores define a second dimension greater than the first dimension.

30. The method of claim 25, wherein guiding a plurality of first instruments includes guiding at least a micro electrode recorder and guiding a second instrument includes guiding a deep brain stimulation probe.

31. The method of claim 25, wherein guiding a plurality of first instruments or guiding a second instrument includes at least one of guiding a micro-electrode, guiding a deep brain stimulation probe, guiding a cannula, guiding a biopsy needle, guiding a seed implant device, guiding a catheter, guiding an ablation device, or combinations thereof.

32. The method of claim 25, further comprising:
recording electrical activity within the selected portion of the anatomy with at least one of the first instruments;
providing a therapy to the selected portion of the anatomy with the guided second instrument.

33. The method of claim 25, further comprising:
obtaining image data of the selected portion of the anatomy;
determining a planned trajectory to reach the selected portion of the anatomy; and
supporting a drive system relative to the selected portion of the anatomy.

34. The method of claim 33, wherein obtaining image data includes obtaining x-ray image data, obtaining computer aided tomography image data, obtaining magnetic resonance image data, obtaining PET image data, obtaining SPECT image data, obtaining ultra sound image data, or combinations thereof.

35. The method of claim 25, wherein moving a sub-plurality of guide members transverse to the instrument axes includes moving the sub-plurality of guide members perpendicular to the instrument axes.

* * * * *